United States Patent [19]

Fee et al.

[11] Patent Number: 4,877,506
[45] Date of Patent: Oct. 31, 1989

[54] MONOLITHIC SOLID ELECTROLYTE OXYGEN PUMP

[76] Inventors: Darrell C. Fee, 2529 Lee St., Woodridge, Ill. 60517; Roger B. Poeppel, 67 Stephanie La., Glen Ellyn, Ill. 60137; Timothy E. Easler, 564 N. Pinecrest, Bolingbrook, Ill. 60439; Dennis W. Dees, 6224 Middaugh Ave., Downers Grove, Ill. 60517

[21] Appl. No.: 35,799

[22] Filed: Apr. 8, 1987

[51] Int. Cl.$^4$ ............................................. C25B 9/00
[52] U.S. Cl. ................................... 204/242; 204/410; 429/30; 429/33
[58] Field of Search .................... 204/410, 425, 242; 429/30, 34

[56] References Cited

U.S. PATENT DOCUMENTS

| | | | |
|---|---|---|---|
| 3,400,054 | 9/1968 | Ruka et al. | 204/427 |
| 4,476,196 | 10/1984 | Peoppel et al. | 429/32 |
| 4,476,197 | 10/1984 | Herceg | 429/32 |
| 4,476,198 | 10/1984 | Ackerman et al. | 429/32 |
| 4,510,212 | 4/1985 | Iraini | 429/30 |

Primary Examiner—John F. Niebling
Assistant Examiner—Kathryn Gorgos

[57] ABSTRACT

A multi-layer oxygen pump having a one-piece, monolithic ceramic structure affords high oxygen production per unit weight and volume and is thus particularly adapted for use as a portable oxygen supply. The oxygen pump is comprised of a large number of small cells on the order of 1-2 millimeters in diameter which form the walls of the pump and which are comprised of thin, i.e., 25-50 micrometers, ceramic layers of cell components. The cell components include an air electrode, an oxygen electrode, an electrolyte and interconnection materials. The cell walls form the passages for input air and for exhausting the oxygen which is transferred from a relatively dilute gaseous mixture to a higher concentration by applying a DC voltage across the electrodes so as to ionize the oxygen at the air electrode, whereupon the ionized oxygen travels through the electrolyte and is converted to oxygen gas at the oxygen electrode.

15 Claims, 9 Drawing Sheets

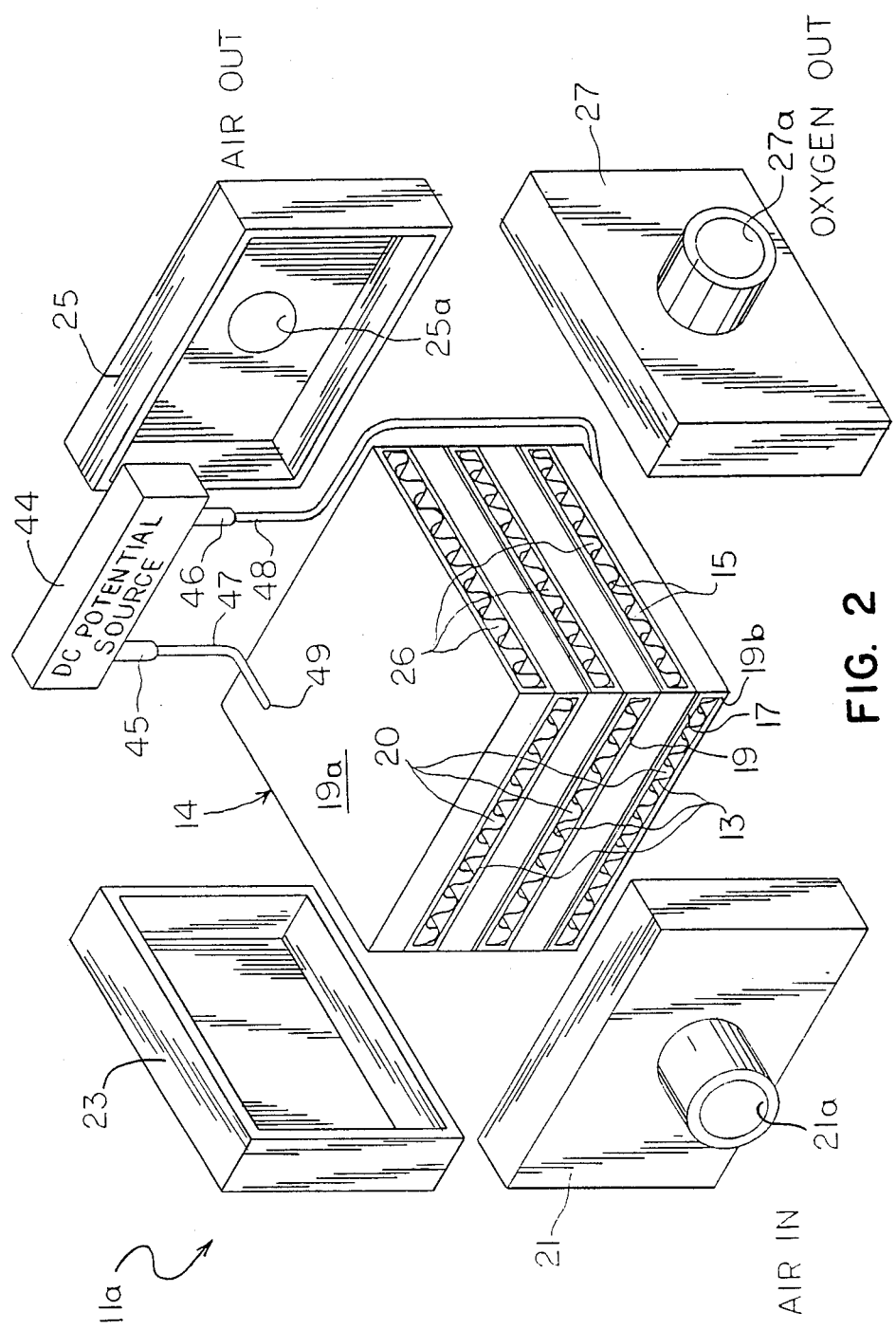

○ CELL REACTIONS:

○ CELL: $O_2(\sim 0.5 \text{ atm}) \rightarrow O_2(\sim 1.0 \text{ atm})$

DIFFUSION LIMITATIONS

APPLIED $E = \dfrac{RT}{nF} \ln \dfrac{P_{O_2},\text{ OXYGEN}}{P_{O_2},\text{ AIR ELECTRODE INTERFACE}}$ $P_{O_2}$, AIR STREAM  EXTRA 63 mV REQUIRED FOR LOW
$P_{O_2}$, INTERFACE $= \dfrac{1}{10} P_{O_2}$, AIR STREAM

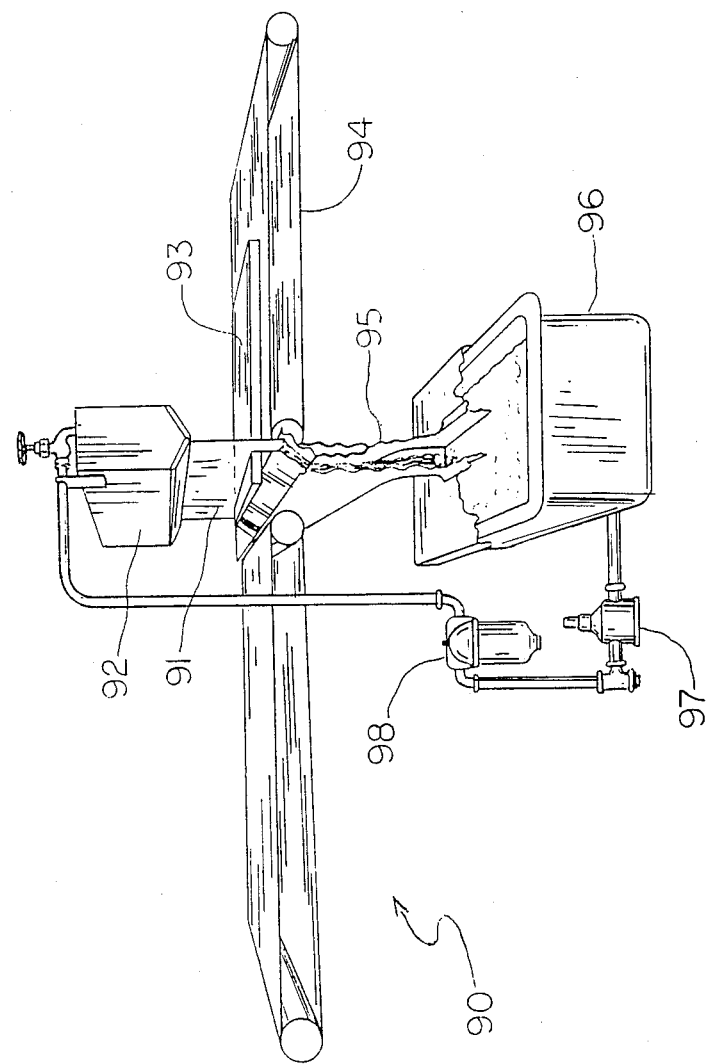

MONOLITHIC SOLID ELECTROLYTE OXYGEN PUMP

CONTRACTUAL ORIGIN OF THE INVENTION

The United States Government has rights in this invention pursuant to Contract No. W-31-109-ENG-38 between the U.S. Department of Energy and the University of Chicago representing Argonne National Laboratory.

BACKGROUND OF THE INVENTION

This invention relates generally to the removal of oxygen from air or other dilute source to form a higher concentration of oxygen and is particularly directed to an electrically operated, structurally monolithic oxygen pump for transferring oxygen across a solid electrolyte barrier to form a higher concentration of oxygen.

Present methods of removing oxygen from air or other dilute sources of oxygen involve pumped cryogenic distillation, preferential absorption-desorption under conditions of temperature and/or pressure cycling, or the electrolysis of water. Pumped cryogenic distillation is particularly adapted for supplying large quantities of oxygen and is impractical as an oxygen source where only a limited quantity of oxygen is desired. Preferential absorption-desorption in combination with temperature and/or pressure cycling typically requires an elaborate array of valves and other controls in conjunction with mechanical compressors or pumps and/or heaters and thus represents a complex and somewhat expensive approach to oxygen production. Producing oxygen by the electrolysis of water also results in the production of hydrogen as a by-product. The volatility of the hydrogen thus produced requires extensive safety measures to be adopted rendering this approach more expensive and complex.

Attempts to design a portable, low cost source of oxygen of reduced complexity capable of producing oxygen in relatively high concentration have met with limited success. Performance requirements for a portable oxygen pump are measured in terms of oxygen enrichment, air utilization, cell and array voltage, operating temperature and lifetime, thermal and mechanical shock, startup and shutdown, power cycling, monitoring and control, and geometry or the conformance of the shape of the oxygen source to the particular requirements of a portable application. These performance requirements are typically competing and, in some cases, appear to be mutually exclusive as evidenced by the unsuccessful prior attempts to develop an efficient, portable, low cost and highly reliable source of oxygen capable of producing oxygen in relatively high concentrations. The present invention, however, represents an improvement over prior art efforts in this area in that it affords a monolithic solid electrolyte oxygen pump which is reliable, rugged, easily started up and controlled as well as shut down. The monolithic solid electrolyte oxygen pump of the present invention operates at relatively low temperatures, does not produce hazardous by-products, and is capable of producing oxygen in relatively high concentrations.

OBJECTS AND SUMMARY OF THE INVENTION

Accordingly, it is an object of the present invention to provide a low cost, efficient, portable oxygen pump.

It is another object of the present invention to provide an electrically operated, structurally monolithic, solid electrolyte oxygen pump for transferring oxygen across a solid electrolyte barrier from a relatively dilute gaseous mixture to a higher concentration.

Yet another object of the present invention is to provide a safer means and method for increasing the oxygen concentration of a gas which involves neither the generation of pure oxygen nor the production of an explosive gas such as hydrogen.

A further object of the present invention is to provide an electrically operated solid oxide oxygen pump for transferring oxygen from air or another dilute oxygen source across a solid electrolyte in forming a gas having a higher oxygen concentration.

A still further object of the present invention is to provide an improved source of oxygen including a plurality of electrically interconnected pumps each having a plurality of chambers or passages to allow for the flow of air and oxygen therein.

Still another object of the present invention is to provide an improved oxygen pump capable of very high oxygen output per unit mass and volume using a strong and lightweight honeycomb structure comprised of a large number of small cells.

The present invention contemplates an electrical oxygen pump for separating oxygen from a mixture of oxygen and at least one other gaseous component. The oxygen pump includes a thin elongated solid electrolyte wall preferably comprised of yttria stabilized zirconia which is disposed between a pair of electrodes which are preferably comprised of porous lanthanum manganites, such as $LaMnO_3$, and further includes connecting walls of dense lanthanum manganites. The oxygen pump is comprised of a plurality of interconnecting cells and chambers on opposite sides of the cells to respectively provide for a source of air and the collection of oxygen. Each cell thus includes a solid electrolyte wall and a pair of the electrodes on opposite sides of the electrolyte with an interconnecting wall disposed between and coupled to adjacent cells. A source of DC voltage is applied to the electrodes such that oxygen is ionized at the first electrode, travels through the electrolyte, and is converted to oxygen gas at the second electrode. The oxygen pump of the present invention is lightweight, may be utilized as a portable device which may be operated on a 12 volt or other battery, and is capable of producing oxygen without the extensive equipment or dangers associated with other oxygen separators or generators.

BRIEF DESCRIPTION OF THE DRAWINGS

The appended claims set forth those novel features which characterize the invention. However, the invention itself, as well as further objects and advantages thereof, will best be understood by reference to the following detailed description of a preferred embodiment taken in conjunction with the accompanying drawings, where like reference characters identify like elements throughout the various figures, in which:

FIG. 2 is an exploded perspective view of another embodiment of an oxygen pump in accordance with the present invention illustrating additional details thereof;

FIG. 12 is a simplified schematic diagram of a curtain coating process for forming corrugated shapes in an initial casting as contemplated for use in practicing the present invention; an FIG. 13 is a simplified schematic illustration of another ceramic forming technique which could be used in the fabrication of multilayer arrays with gas flow channels involving calendering (also referred to as roll-forming) for use in fabricating an oxygen pump in accordance with the present invention.

DESCRIPTION OF PREFERRED EMBODIMENT

Figure 1B:
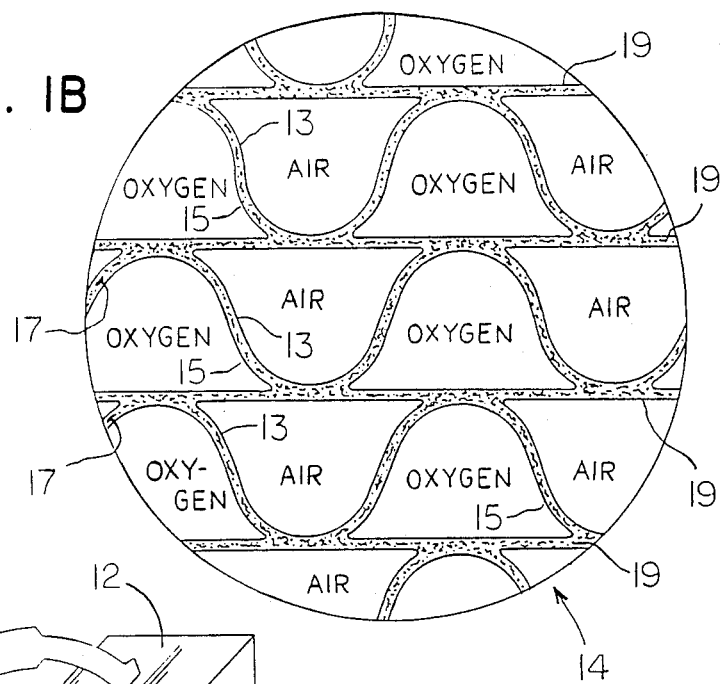
FIG. 1 is a simplified combined perspective and sectional view of one embodiment of an oxygen pump in accordance with the present invention.
Figure 1A:
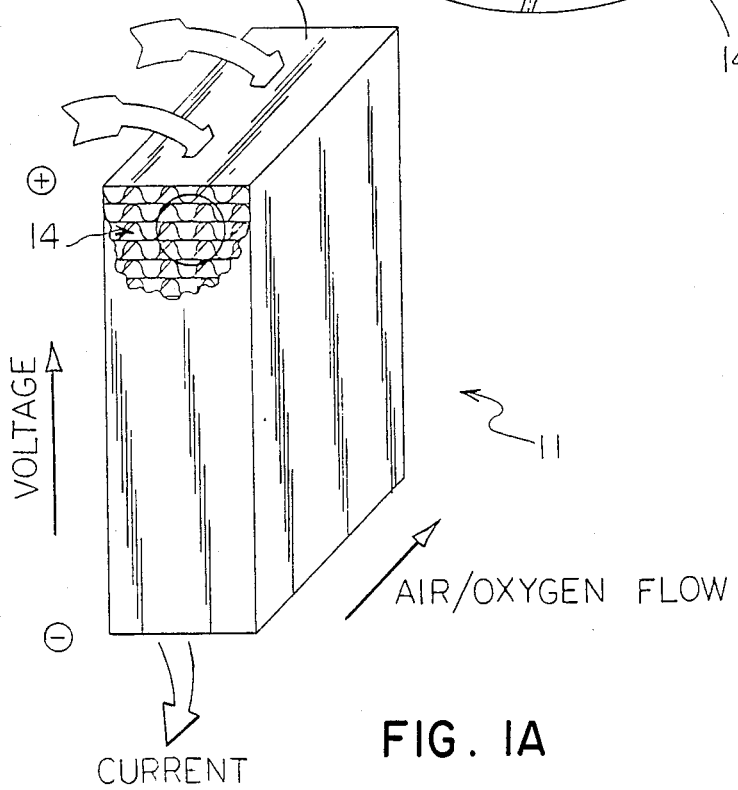

Referring to FIG. 1, there is shown a partially cut-away perspective view as well as an enlarged sectional view of a monolithic solid oxide oxygen pump 11 in accordance with the principles of the present invention. The oxygen pump 11 includes a housing 12 within which is disposed a honeycomb core 14 shown in greater detail in the enlarged sectional view illustrated in FIG. 1. The honeycomb core 14 is comprised of a large number of small cells on the order of 1-2 millimeters in diameter, with the walls of the honeycomb structure formed of a thin, e.g., 25-50 micrometers, ceramic layer of cell components including an air electrode 13, an oxygen electrode 15, an electrolyte 17, and an interconnecting structure or interconnection materials 19. The aforementioned structures form passages for input air which flows in the direction of the arrow in the figure. These structures also form the passages for exhausting the oxygen which is formed as described below. A suitable intake or inlet aperture as well as appropriate output or outlet apertures are provided in the housing 12 to allow for a continuous stream of input gas having a relatively low oxygen content to flow through the honeycomb core 14 and to allow the separated oxygen as well as the reduced intake gas to be removed or exhausted from the housing. In the honeycomb core, the plurality of spaced cells each comprised of an air electrode 13, an oxygen electrode 15 and an electrolyte 17 disposed therebetween and in contact therewith are arranged in a stacked array. The interconnection materials 19 are disposed between and in contact with adjacent cells of the oxygen pump.

Referring to FIG. 2, there is shown an exploded perspective view of another embodiment of an oxygen pump 11a in accordance with the present invention. The electrolyte 17 as well as the air electrode, or cathode, 13, and the oxygen electrode, or anode, 15 are adapted for the monolithic solid electrolyte, or oxide, oxygen pump 11a of the present invention from earlier efforts with regard to monolithic fuel cells as disclosed in U.S. Pat. Nos. 4,476,196 to Poeppel et al and 4,476,198 to Ackerman which are both assigned to the assignee of the present application.

The core 14 is a one piece assembly having a generally rectangular parallelepiped shape with two sets of opposite side faces rotated approximately 90° from one another and opposite top and bottom faces at approximately 90° from the side faces. Passageways 20 and 26 extend through the core 14 between the opposite side faces and are oriented generally transversely. Structures 23 and 27 adjacent opposite side faces of the core 14 define spaced manifolds which communicate with one another via passageways 26 formed in the core. Further, structures 21 and 25 adjacent the other side faces of the core 14 also define spaced manifolds that communicate with one another via passageways 20 formed in the core. An inlet line 21a in manifold structure 21 is adapted to carry air or another oxygen bearing gas to the core manifold for flow through the passageways 20. The oxygen is removed from the inlet air within the core 14 and is directed into the second set of passageways 26 for removal from the core via an outlet line 27a in structure 27. The residual gas which is low in oxygen content continues through the first set of passageways 20 and is removed from the outlet manifold 25 via another outlet line 25a. The first and second sets of passageways 20 and 26 are disposed transverse to one another, so that the oxygen is removed from the intake air in a direction generally 90° relative to the intake air flow. Each of the manifold structures 21, 23, 25 and 27 is adapted for tight fitting placement upon a lateral surface of the core 14 and is maintained in position thereon by conventional means such as a ceramic paste, or the like, to minimize leakage of the gases between the inlet manifold and the two outlet manifolds. A generally box-like outer structure may be positioned around the oxygen pump 11a so as to completely enclose it except for the three gas carrying lines. An outer housing which could be easily adapted for completely enclosing the oxygen pump 11a is disclosed in the aforementioned U.S. Pat. No. 4,476,196. A DC voltage may be applied across the core 14 by connecting a first external terminal 45 to an upper surface of the core by means of the combination of a first conductor 47 and first contact 49 and by further connecting a lower surface of the core to a second external terminal 46 via a second conductor 48 and contact (not shown). By connecting the first and second external terminals 45, 46 to a DC potential source 44, a DC voltage may be applied in a generally vertical direction across the core 14 such as shown by the direction of the arrow in FIG. 1. It should be pointed out here that the present invention contemplates virtually any relative angle between the air and oxygen flow channels. For example, FIG. 1 illustrates the air and oxygen flow channels as aligned, or parallel, while FIG. 2 shows these two sets of gas flow channels as oriented at 90° relative to each other. Although FIG. 2 depicts a stacked array of solid electrolyte oxygen pump cells of the present invention, a single oxygen pump comprised of a pair of electrodes, an electrolyte disposed therebetween, and a pair of interconnect layers each positioned in contact with a respective electrode will also produce oxygen in accordance with the principles of the present invention.

Figure 3:
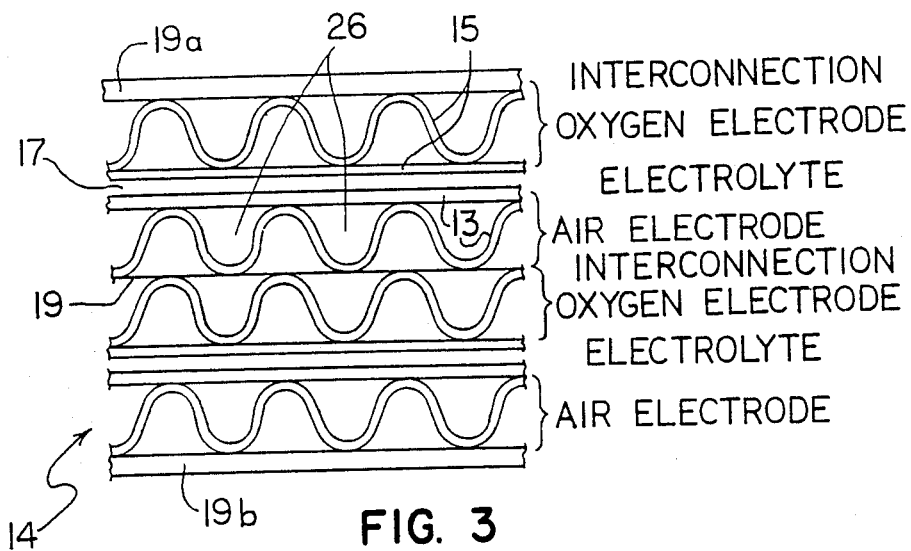
FIG. 3 is a sectional view of the oxygen pump of FIG. 2.

Referring to FIG. 3, there is shown a diagonal sectional view of a portion of the core of the oxygen pump of FIG. 2. Each air electrode, or cathode, 13 and each oxygen electrode, or anode, 15 is sandwiched at spaced opposing sides between electrolyte material 17 and interconnect material 19. These composite anode and cathode wall structures are thus alternately stacked on one another and are separated by an electrolyte 17 or interconnect 19 (typically being a single common layer), whereby the inlet air and oxygen passageways are disposed transverse to one another such as illustrated in FIG. 2.

Thus, on one side, the oxygen electrode 15 is separated from the air electrode 13 by a thin layer of electrolyte material 17 to form an electrolyte wall. This also defines a "cell" and the applied DC voltage will occur across the electrolyte 17 between electrodes 13 and 15. On the other side, the air electrode (cathode) 13 and the oxygen electrode (anode) 15 are separated by a generally thin layer of interconnect material 19 to form an interconnect wall. The interconnection 19 serves to isolate the inlet air and outlet oxygen gases from one another, and also serves to electrically connect together the anode electrode of one cell and the cathode electrode of an immediately adjacent cell. This arrangement thus provides a series circuit with adjacent cells and allows a DC voltage to be applied across each parallel set of generally planar passageways.

In the oxygen pump of the present invention, many such serially connected anode-cathode cell combinations, perhaps as many as several hundred, could be provided to maximize the output of the thus produced oxygen. The outermost interconnections 19a and 19b respectively located at the upper and lower portions of the core 14 are connected electrically via the aforementioned first and second contacts, first and second conductors 47, 48, and first and second external terminals 45 and 46, each of which is coupled to a common DC voltage source, which is not shown for simplicity.

Figure 4:
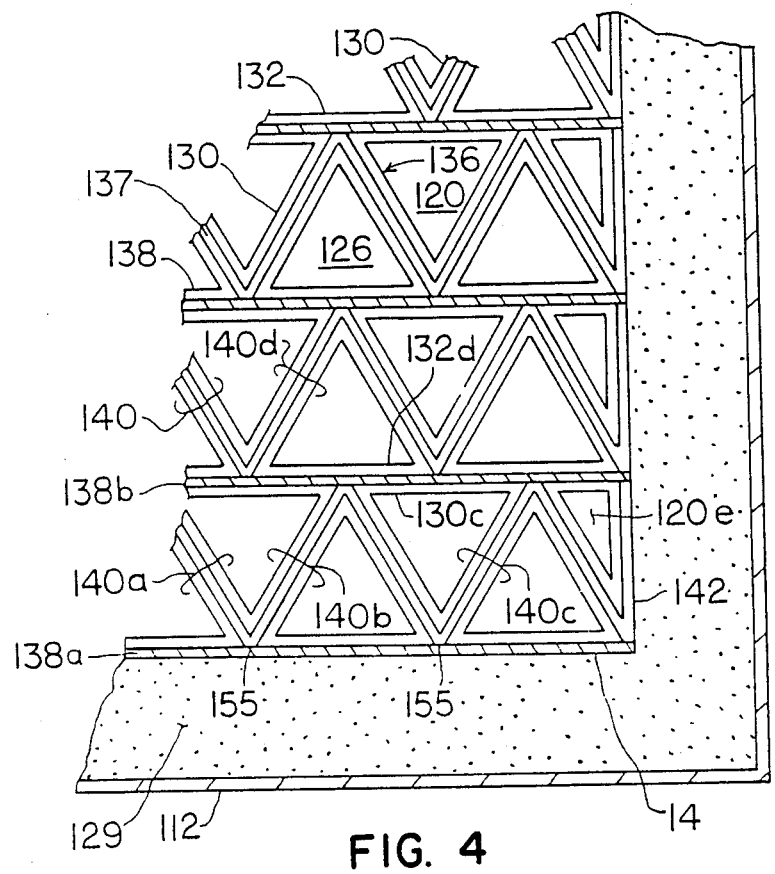
FIG. 4 is an enlarged cross sectional view of the embodiment of an oxygen pump of FIG. 1.

FIG. 4 illustrates an enlarged cross section of a preferred embodiment of the core 14 of the oxygen pump 11 of FIG. 1. The passageways 120 for the intake air are formed with only cathode material 130 defining the exposed passageways walls, while the passageways 126 for the separated oxygen are formed with only anode material 132 defining the exposed passageways walls. Adjacent cell passageways 120 and 126 are further separated by either or both an electrolyte wall portion 136 and by an interconnect wall portion 138. The electrolyte wall portion 136 provides a thin layer of electrolyte material 137 between the cathode material 130 and the anode material 132. The interconnect wall portion provides a thin layer of interconnect material 138b between the cathode and anode materials 130 and 132. The intake air would be conveyed from a source (not shown) to a manifold for flow through the passageways 120 in the core 14 toward an outlet manifold.

A DC electrical potential is applied between the cathode 130 and the anode 132 and across the electrolyte 137. This combination of three elements thus defines a "cell" 140 in the overall oxygen pump. In addition, for all of the electrolyte walls thus confined between any pair of adjacent interconnect walls (138a, 138b, for example), there is an in-parallel electrical hookup of these cells (140a, 140b, for example). On the other hand, each interconnect wall (138b, for example) disposed between the separate cells above and below it (cells 140c and 140d, for example) electrically connects the cathode of one cell with the anode of the adjacent cell (cathode 130c with anode 132d, for example). This provides for an in-series hookup of the cells (140c and 140d, for example) on the opposite sides of the interconnect wall 138b. The electrolyte walls 136 are alternated or backfolded in effect between the interconnect walls 138 so that the air and oxygen passageways 120 and 126 are likewise alternately disposed between any pair of adjacent interconnect walls. At the side edge of the core 14, a neutral wall 142 will typically be used to define the boundary for the end inlet air passageway 120e, the neutral wall having only the cathode material and the electrolyte extended between the adjacent interconnect walls 138a and 138b, for example.

The cathode 130 and the anode 132 within the electrolyte walls 136 are porous to the degree required to allow the oxygen removed from the intake air to pass therethrough, while the electrolyte 137 and the interconnect 138 are impervious and serve to isolate the inlet air and the oxygen completely from one another. Likewise, the electrolyte walls 136 are electronically not conductive as between the cathode and anode formed on opposite sides thereof, but the electrolyte does provide ionic conductivity. The cathode and anode are comprised of conductive materials, while the interconnect walls electrically connect the anode and cathode of the cells on opposite sides of the wall in series with one another.

The fuel cell core 14 is formed as a monolithic or rigid array of cells 140. In addition, the core 14 is formed solely or entirely of the active cathode, anode, electrolyte and interconnect materials 130, 132, 137 and 138b, respectively. Thus, nonactive materials are not used in the oxygen pump of the present invention for support of the passageways 120 and 126. Each active material is in the form of a thin layer, with the layers integrally bonded or fused together to form the monolithic core 14. The core walls 136 and 138 (and 142) immediately adjacent to and defining the air and oxygen passageways 120 and 126 are quite short or of small spans to provide that the passageways themselves are of small cross section (perhaps as small as several square millimeters). Because of the small wall spans, the thin layered materials each totaling only fractions of a millimeter in thickness will be structurally sufficient to support the core 14 and any gas and pressure differential loads required.

The embodiment of the monolithic core 14 illustrated in FIG. 4 provides an effective ratio of the area of the electrolyte walls 136 to the interconnect walls 138 (or as a percentage of the cross sectional area of the cell passageways) to produce efficient removal of oxygen from the inlet air. The electrolyte walls 136 are angled alternately or backfolded on one another between the adjacent parallel pairs of interconnect walls 138 to define alternately inverted triangularly shaped inlet air passageways 120 and oxygen passageways 126 between the interconnect walls, where the passageways 120 and 126 extend in side-by-side parallel relation to one another. In the illustrated embodiment, the interconnect walls 138 are basically flat or planar, while the electrolyte walls 136 may be either flat or curved, the electrolyte walls of each passageway being angled and meeting the interconnect walls 138 at corner junctures 155 generally disposed along and spaced apart on any one interconnect wall. The percentage of active electrolyte wall surface area interposed between each inlet air passageway and oxygen passageway 126 is quite high, compared to the area of the passageways. Moreover, the triangularly arranged passageways provide a compact design. Again, the monolithic core 14 is formed only of the active anode, cathode, electrolyte and interconnect materials, each as very thin layers, and no nonactive materials are present for support. A space between the core 14 and an outer housing 112 is packed as at 129 with a ceramic powder or the like to minimize leakage of the gases.

Figure 5:
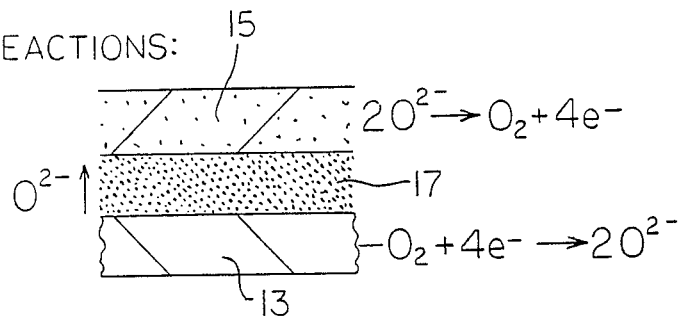
FIG. 5 is a sectional view of a portion of the oxygen pump of the present invention which illustrates the reactions taking place in various portions of a cell in the oxygen pump.

Referring to FIG. 5, there is shown a sectional view of a portion of the oxygen pump illustrating the reactions which occur in the pump. The dense electrolyte layer 17 is sandwiched between the forced air electrode (cathode) 13 and the porous oxygen electrode (anode) 15. At the air electrode 13, oxygen in the air accepts electrons from the external circuit which applies the DC voltage across the oxygen pump to form oxide ions. The oxide ions are driven through the electrolyte layer 17 and away from the air electrode 13 by the applied voltage. At the oxygen electrode 15, the oxide ions coming from the electrolyte 17 give up electrons in forming oxygen gas in the stacked cell array. The aforementioned interconnection layer, which is not illustrated in FIG. 5 for simplicity, carries the electrons from the oxygen electrode 15 of one cell to the air electrode 13 of the next adjacent cell in electrical series. The interconnection layer, or bipolar plate, is dense, similar to the electrolyte layer 17, in order to physically separate the air and oxygen gases.

The minimum applied voltage to separate oxygen can be determined from thermodynamic considerations using the Nernst equation of:

$$E = \frac{RT}{nF} \ln \frac{P_{O_2} \text{ (oxygen enriched stream)}}{P_{O_2} \text{ (air stream)}}$$

where
 P is pressure (atom),
 R is the gas constant (8.317 Joule $K^{-1}$ $mol^{-1}$,
 T is temperature (K),
 n is the number of electrons transferred (four for oxygen molecules), and
 F is Faraday's constant (96,585 coulombs/equivalent).

As oxygen is removed from the air stream, the partial oxygen pressure $PO_2$ in the air stream is reduced such that the minimum applied voltage required to separate the oxygen increases representing an important limitation in the operation of the oxygen pump. The anode and cathode of each oxygen pump cell are good electronic conductors and thus act as isopotential surfaces. Thus, the actual applied cell voltage must be no less than the theoretically required cell voltage at the lowest oxygen concentration in the air stream. The difference between the applied voltage and the maximum required theoretical voltage is the power wasted in internal resistance losses. As a result of its lower internal resistance, the monolithic oxygen pump cells of the present invention can be operated at higher current density than conventional cells, yet achieve the same output efficiency.

Figure 6:
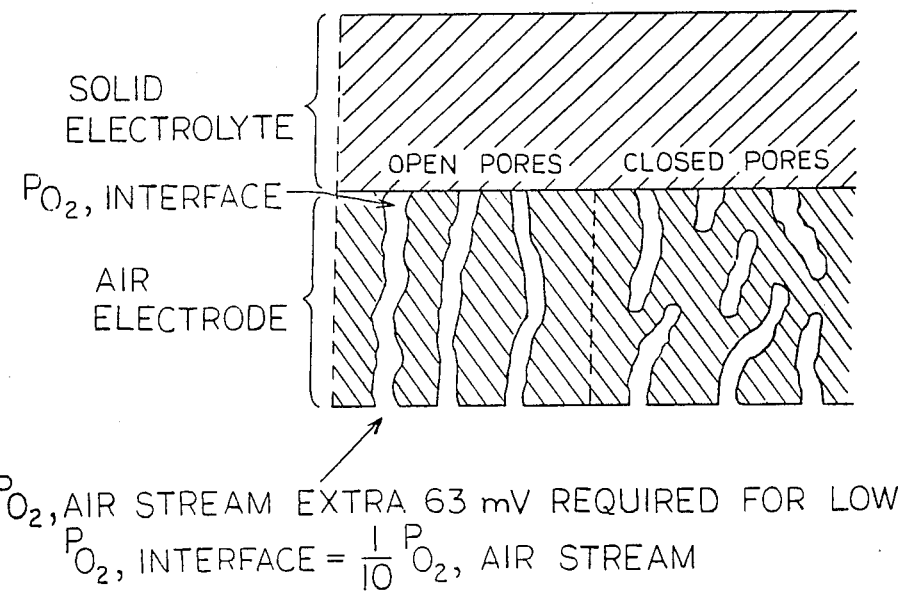
FIG. 6 is a sectional view of a portion of the oxygen pump of the present invention illustrating the details of gas diffusion therein.

The monolithic oxygen pump of the present invention minimizes diffusion losses by employing thin electrodes. Diffusion of the oxygen through the electrode may limit the performance of thick electrodes. In the air stream, oxygen must diffuse at right angles from the flow in the cell's air channels through the electrode structure and to the reaction sites. The oxygen diffuses through the electrode and reacts at (or near) the three-phase boundary of gas, electrode, and electrolyte. There the oxygen is consumed at a rate equal to the electrochemical reaction. The partial pressure of the oxygen is less at the actual reaction site than in the adjacent gas stream. The reduced oxygen partial pressure at the interface, $P_{O_2\ eff}$, increases the cell voltage as shown by the Nernst equation. The cell voltage is determined from the Nernst equation using the pressure of the oxygen at the electrode/electrolyte interfaces, as shown in FIG. 6. Thus, the reduced oxygen pressure at the reaction site represents an increase in the voltage (which must be applied to separate oxygen), of $RT/nF$ ln $P_{O_2\ eff}/P_{O_2\ gas}$, where $P_{O_2\ gas}$ is the oxygen partial pressure in the bulk gas stream and $P_{O_2\ eff}/P_{O_2\ gas}$ is the partial pressure ratio of oxygen necessary to transport oxygen through the electrode at whatever rate is required by the current being generated. The monolithic array design of the present invention thus minimizes diffusion losses by employing thin electrodes.

In addition to gas diffusion limitations, there is a potential barrier to charge transport across phase boundaries between the electrode and the electrolyte that is associated with the electrochemical half cell reactions. The voltage loss due to this barrier is called "activation", or "surface", overpotential. It decreases as the electrochemical reaction kinetics become more rapid. It increases as the current density (current per unit area) increases, usually in a much less than linear fashion. It is every bit as complex as the detailed chemical and electrochemical kinetic mechanism. Fortunately, reaction rates are very rapid at the operating temperature of the oxide oxygen pump, so it is not necessary to provide very thick electrodes to assure sufficient surface area, and activation overpotential is not a major consideration on the monolithic design.

Figure 7:
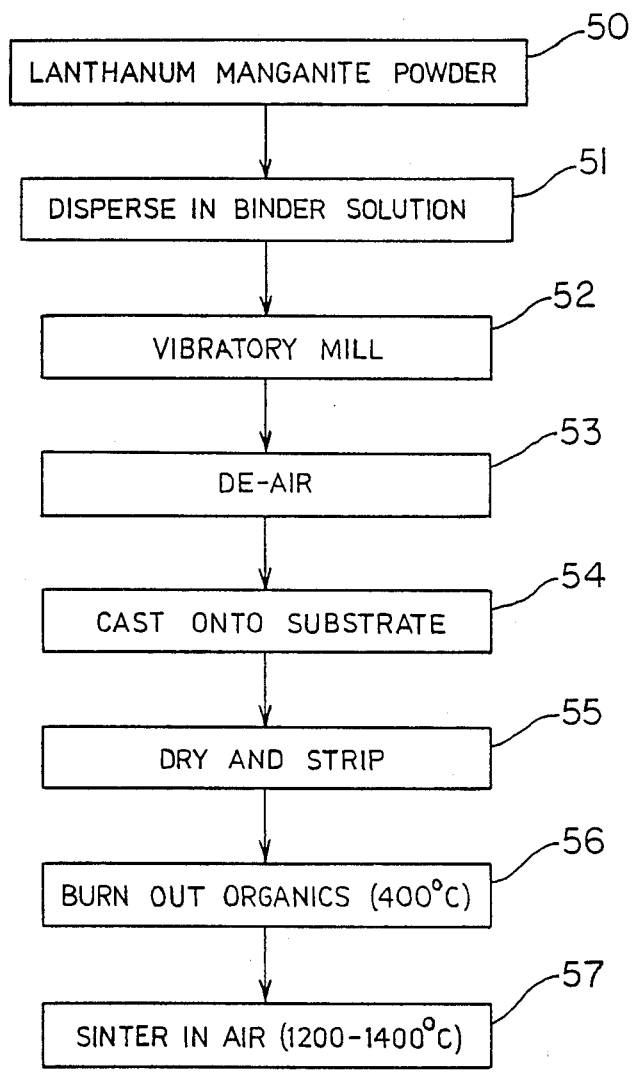
FIG. 7 is a flow chart illustrating a method for fabricating a portion of an oxygen pump in accordance with the present invention.
Figure 8:
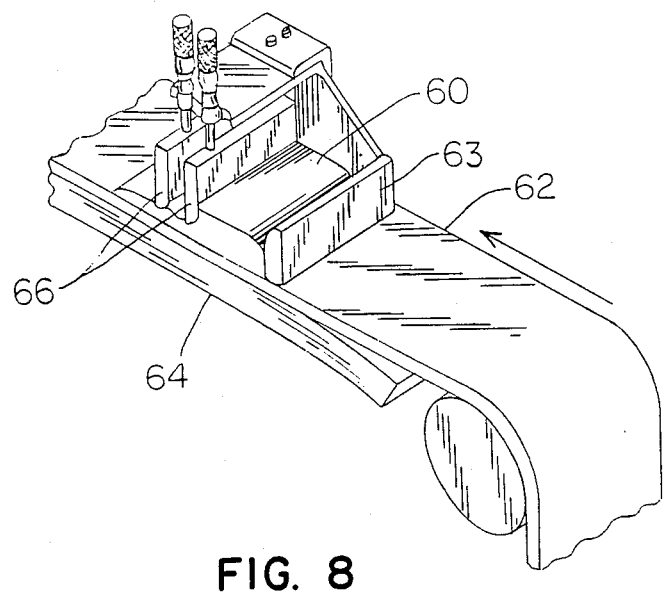
FIG. 8 is a perspective view of an arrangement for fabricating a portion of the oxygen pump of the present invention.
Figure 9:
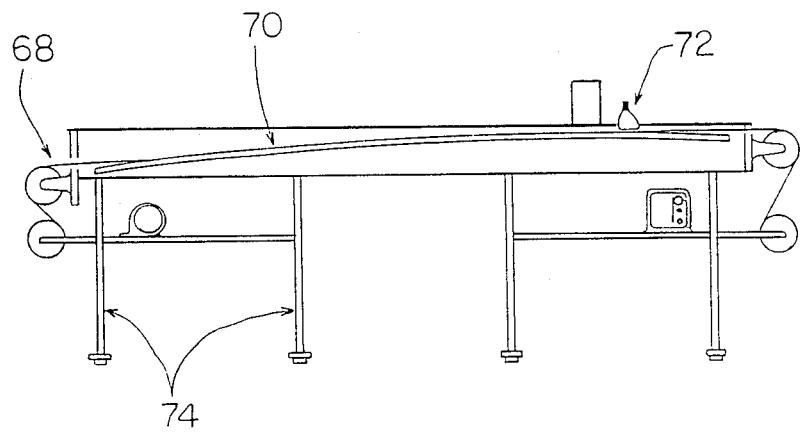
FIG. 9 illustrates an arrangement for leveling a ceramic tape as used in the fabrication of an oxygen pump of the present invention.

Referring to FIG. 7, there is shown in the form of a flow chart the steps involved in forming thin ceramic layers for use in the oxygen pump of the present invention using commercially proven fabrication methodology. FIGS. 8 and 9 are simplified schematic diagrams of tape casting apparatus which could be used in carrying out the process set forth in FIG. 7. Tape casting is a forming technique which is ideally suited for the fabrication of ceramics into thin (0.025-0.75 millimeter) sheets of large area. Tape casting is used commercially to form ceramic capacitor plates which are on the order of 0.025 millimeter in thickness as well as ceramic substrates and piezoelectric materials. The process for forming the thin ceramic layers begins with providing a ceramic powder such as comprised of lanthanum manganite powder at step 50 and dispersing the ceramic powder mixture into an organic or aqueous solvent containing organic binders and plasticizers to form a slurry or slip at step 51. The desired particle size, i.e., 1-2 micrometers in diameter, must be maintained in the slurry prior to tape casting. The ceramic powders tend to agglomerate into large chunks. Energy is provided by a vibratory mill at step 52 to break up the agglomerates. After milling, the slip is de-aired at step 53 to remove bubbles before tape casting. The solvent lost during the de-airing step is minimized so as to avoid undesirable "skinning" on the surface of the slip resulting in poor performance during tape casting.

Following de-airing, the slip is cast onto a suitable substrate at step 54. An arrangement for casting of the slurry onto a substrate is described below. After drying, the tape is stripped from the substrate at step 55 prior to firing. The substrate is selected to be compatible with the solvent/binder/dispersant system of the tape to promote ease of removal. The firing operation begins at step 56 with a low temperature step at approximately 400° C. to burn out the organics. The second step in the burnout process involves high temperature heating, e.g., in the range of 1200°–1400° C., sintering of the tape in air at step 57. Adequate time is provided at steps 56 and 57 to allow the gases being formed to diffuse away from the tapes without affecting the chemical or structural integrity of the ceramic materials.

Apparatus for the casting of the slurry or slip into a suitable substrate and leveling it to the desired thickness is shown in FIGS. 8 and 9. In FIG. 8, the slip 60 is positioned upon and transported by a carrier film 62 which, in turn, is supported by a tempered glass bed 64. With the carrier film 62 displaced in the direction of the arrow in the figure, the slip is maintained in position on the carrier film by a retaining bracket 63 so as to displace the slip with respect to and in contact with a pair of doctor blades 66 which level the slip to the desired thickness.

Referring to FIG. 9, there is shown another arrangement for transporting and leveling the slip. In the arrangement of FIG. 9, the carrier film 68 is transported over and supported by a curved tempered plate glass bed 70. A doctor blade 72 disposed immediately adjacent to and above the thus transported carrier film provides for the desired leveling of the transported slurry to the desired thickness. The curved tempered plate glass bed 70 is mounted to a suitable support frame which includes a sturdy, levelable table base 74.

Figure 10:
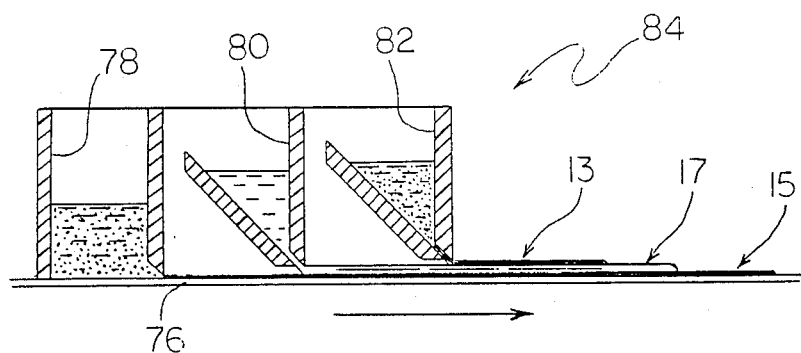
FIG. 10 is a simplified schematic diagram of a multilayered tape casting process used in fabricating a portion of the oxygen pump of the present invention.

Referring to FIG. 10, there is shown a simplified schematic of an arrangement for sequential tape casting used in a preferred process for fabricating the monolithic oxygen pump of the present invention. The sequential tape casting apparatus 84 is disposed in closely spaced arrangement above a linearly displaced carrier film 76. The sequential tape casting apparatus 84 includes first, second and third containers/dispensers 78, 80 and 82 arranged in a generally linear array immediately above the carrier film 76 and aligned along the direction of transport thereof. The anode material 15 is positioned within the first container/dispenser 78, the electrolyte 17 is positioned within the second container/dispenser 80, and the cathode material is positioned within the third container/dispenser 82. Each of the container/dispensers is provided with an appropriate aperture immediately adjacent to and above the moving carrier film 76 to allow for the sequential deposit of its contents in a thin film upon the carrier film as it is linearly transported. Thus, the anode 15 is deposited in the form of a thin layer on the upper surface of the moving carrier film 76, the electrolyte 17 is deposited on the upper surface of the thus deposited anode, and the cathode 13 is deposited on the upper surface of the thus deposited electrolyte. A similar structure may be fabricated comprised of an anode, interconnection material, and a cathode. The various materials are selected and treated to give the same lateral shrinkage during firing.

In the tape casting approach, the unfired ceramic layers must be folded into a corrugated cross section to form the gas flow channels in the cell array. Similar techniques have been developed and patented in the fabrication of monolithic ceramics, most often of a single material. U.S. Pat. No. 3,112,184 to Hollenbach discloses a process for forming a thin walled corrugated structure of silicate-based ceramics by dip coating a ceramic slurry onto natural cellulose paper. A simplified schematic diagram of this type of process is illustrated in FIG. 11.

Figure 11:
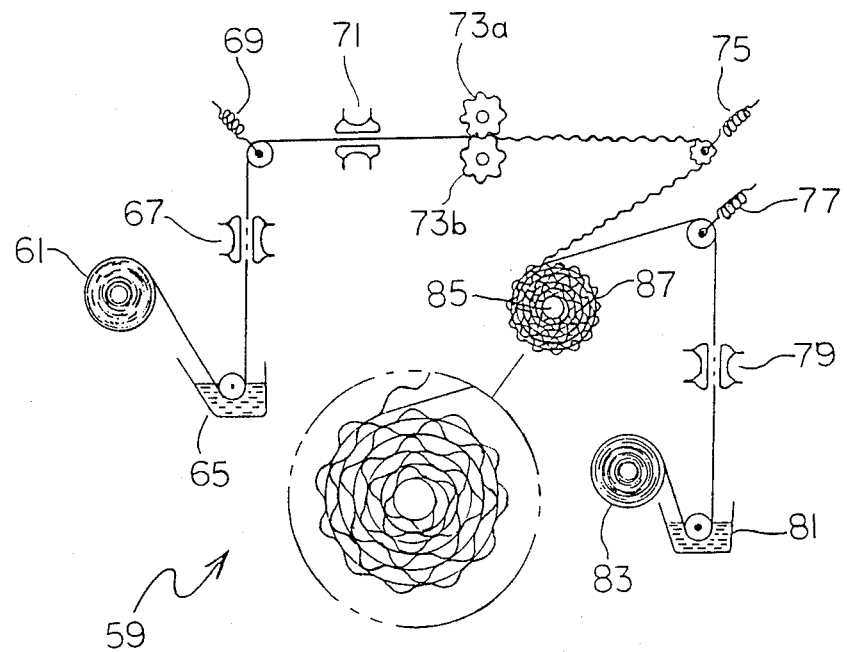
FIG. 11 is a simplified schematic diagram of a process for forming a thin-walled corrugated structure of silicate-based ceramics by dip coating a ceramic slurry onto natural cellulose paper as used in fabricating a portion of the oxygen pump of the present invention.

Referring to FIG. 11, there is shown apparatus 59 for forming a thin-walled corrugated structure of silicate-based ceramics by dip coating a ceramic slurry onto natural cellulose paper. A first cellulose paper roll 61 is unrolled and the cellulose paper thereon is passed through a first ceramic slurry 65. The ceramic slurry is comprised of a ceramic powder dispersed in toluene-butyl alcohol solvent containing an epoxy binder with a hardener. The combination cellulose paper and silicate-based ceramic is then heated by a first heater 67 to a high enough temperature to melt and drive off the cellulose paper. The ceramic strip is then passed around a first tensioner 69 and then through a second heater 71 which heats the ceramic to a temperature at which it is deformable. The ceramic strip is then passed between a pair of corrugation rollers 73a and 73b which crimp the ceramic strip or ribbon at 180° C. into a corrugated cross section of approximately triangular shape with a base of 2.54 millimeters and a height of 1.78 millimeters. A second cellulose paper roll 83 is unrolled and directed through a second ceramic slurry 81 for forming a second thin-walled structure of silicate-based ceramics by coating the ceramic slurry onto the natural cellulose paper as it is unrolled. The ceramic/cellulose paper strip is then passed through a third heater 79 for heating and removal of the cellulose paper therefrom. The second ceramic strip is then passed around a third tensioner 77, while the first ceramic strip is passed around a second tensioner 75, and both ceramic strips are rolled onto an annular cylinder 85 so as to form a monolithic honeycomb ceramic structure on the cylinder. An enlarged view of the monolithic honeycomb ceramic structure is also provided in FIG. 11. By thus laminating a first coated and corrugated ceramic strip with a second uncorrugated coated ceramic strip, a honeycomb ceramic structure with alternate layers of flow channels oriented either perpendicular (cross flow) or parallel (coflow or counterflow) to one another can be produced. Using the known apparatus of FIG. 11 for forming thin-walled corrugated ceramic structures, a monolithic honeycomb ceramic structure has been produced having approximately 62 channels per $cm^2$, a total available surface area of 50 $cm^2/cm^3$, and an 80% open channel area normal to the axis of the annular cylinder 85.

Referring to FIG. 12, there is shown a curtain coating system 90 for forming corrugated shapes in the initial casting, rather than initially flat sheets which are subsequently corrugated. The first step in operation of the curtain coating system 90 involves forcing a liquid slip through a narrow orifice slit in a lower portion of a coating head 92 to form a falling pressure curtain 91 of coating material. The substrate 93 to be coated is passed under the falling curtain 91 on a conveyor belt 94, resulting in positioning of a coating of precise thickness on the surface of the substrate. Coating material not impinging on the substrate 93 is recycled by means of the combination of a return trough 95, a slurry tank 96, a pump 97, and a filter 98. Precise control of the coating thickness is achieved by controlling the pumping feed rate of the slip curtain 91 and the speed of the transporting conveyor belt 94. Coating thicknesses of less than 0.025 to 0.125 millimeter are achievable. Adjustment of the width of the orifice slit in the coating head 92 via a movable knife edge (not shown) permits variation of the velocity of the falling pressure curtain 91, permitting the application of more uniform coatings on irregular surfaces. In one embodiment, conformal coatings of ceramic slips on a substrate are formed with corrugations or other surface contours. The use of thick film inks used in screen printing of electronic microcircuits allows for control of slip viscosity and fluidity for achieving uniform thicknesses on contoured surfaces. Commercially available organic viscosity control additives are available for this purpose. Thermosetting binder resins are also available to produce a somewhat more rigid structure for easier lamination of multi-cell arrays and improved shape retention during the binder burnout and sintering steps. The curtain coating approach thus offers several advantages in the fabrication of monolithic array designs such as a single step process and easy transition from the active area to manifold.

Figures 13A, 13B, 13C, 13D:
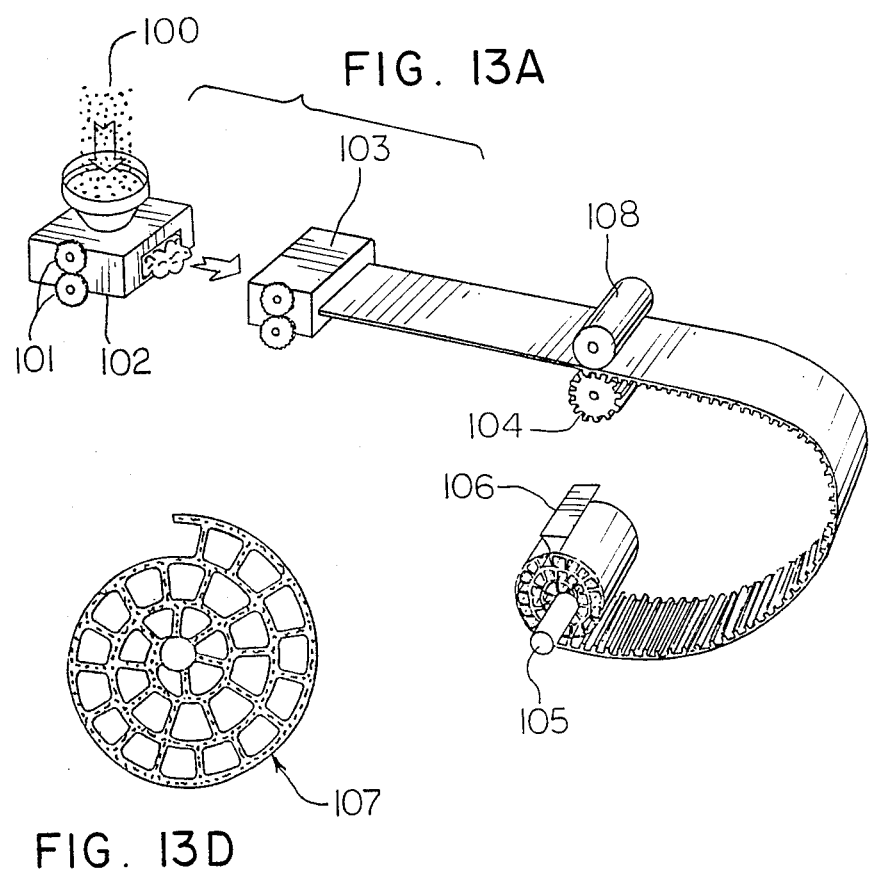

Referring to FIG. 13, there is shown another ceramic forming technique having application in the fabrication of multi-layer ceramic arrays with gas flow channels for use in the present invention which involves a calendering or row-forming system 99. The calendering system 99 includes a mixer and preheater 102 having a hopper into which a ceramic powder and organic carrier mixture 100 is deposited. The mixer and preheater 102 includes a pair of shafts 101 for mixing the ceramic powder and organic carrier and directing the thus formed mixture to a sheet extruder 103. The sheet extruder forms the ceramic powder/organic carrier mix into a thin flat sheet which is then directed between a roller 108 and a bosser 104 for incorporating an array of spaced, parallel ribs on one surface thereof. The ribbed sheet is then rolled onto a support fixture 105 with a heat or solvent bonding applied to its flat surface by means of a heater or applicator 106. The heat or solvent bonding is used to establish good contact between the ribs and the adjoining flat surfaces. The cell geometry of the thus rolled corrugated sheet is shown as element 107 in FIG. 13.

There has thus been shown a monolithic solid electrolyte oxygen pump which includes a solid electrolyte and a pair of electrodes on opposite sides of the electrolyte. Each of the electrodes is shaped so as to form a plurality of respective linear, parallel channels on facing surfaces of the electrolyte, where the channels on one side of the electrolyte may be aligned in parallel with or transversely with respect to the channels on the other side of the electrolyte, or at any angle between these two relative orientation limits. The electrolyte is preferably comprised of an yttria stabilized zirconia, while each of the electrodes is preferably comprised of a porous lanthanum manganite, where the electrode is preferably doped with an approximately 10% portion of the rare earth material. A DC potential is applied between the anode and cathode, whereupon the oxygen is ionized at the cathode, or air electrode, and ionic oxygen migrates through the electrolyte to the anode, or oxygen electrode. The air is thus directed into the channels formed of the air electrode and the oxygen removed from the air passes through the electrolyte and is then removed from the oxygen pump via the channels formed of the oxygen electrode, or anode. A large number of such cells, each comprised of a pair of electrodes and an intermediate electrolyte may be arranged in a stacked array with a DC voltage applied across the multi-cell array for extracting substantial quantities of oxygen from air or another oxygen-bearing gas for use in such applications as purifying the atmosphere as in submarines, as an oxygen generating plant (gasifier), or as a pressure sensitive control such as in fluidonics. Where the oxygen pump cells are arranged in a stacked array, an interconnection or interconnecting material is disposed between immediately adjacent cells. The interconnection material is preferably comprised of a lanthanum manganite which prevents gas flow between immediately adjacent cells. The solid electrolyte and electrodes may be formed as an integral monolithic structure in the form of a series of flat plates separated by a corrugated structure having supporting or interconnection walls which serve to provide an electrical connection between the cells and to isolate the linear, parallel channels formed from the corrugations. The oxygen pump of the present invention is stable in an oxidizing environment, is comprised of materials which are chemically compatible and possess similar coefficients of thermal expansion at the oxygen pump's operating temperature as well as at the much higher temperatures at which these structures are fabricated, provides high electrical conductivity, and can be efficiently and inexpensively produced. The small cell size of the inventive monolithic oxygen pump reduces the voltage losses due to internal resistance which is the principal dissipative loss for the materials (ceramics) and temperatures of interest. The resultant short path for current within the oxygen cells reduces the resistive losses and allows operation at high current densities.

While particular embodiments of the present invention have been shown and described, it will be obvious to those skilled in the art that changes and modifications may be made without departing from the invention in its broader aspects. Therefore, the aim in the appended claims is to cover all such changes and modifications as fall within the true spirit and scope of the invention. The matter set forth in the foregoing description and accompanying drawings is offered by way of illustration only and not as a limitation. The actual scope of the invention is intended to be defined in the following claims when viewed in their proper perspective based on the prior art.

The embodiments of the invention in which an exclusive property or privilege is claimed are defined as follows:

1. An oxygen pump for removing oxygen from an oxygen-bearing gas comprising:
   an anode comprised of a non-oxidizing material and formed of a first corrugated portion and a second planar portion in contact with said first corrugated portion so as to form a first plurality of elongated, generally linear corrugations therein;
   a cathode formed of a third corrugated portion and a fourth planar portion in contact with said third corrugated portion so as to form a second plurality of elongated, generally linear corrugations therein;
   a thin, porous, flat, electrically conductive solid electrolyte having first and second opposed electrode surfaces disposed between and in respective electrical contact with the second planar portion of said anode and with the fourth planar portion of said anode, wherein a first plurality of closed channels is formed between the third corrugated portion and the fourth planar portion of said cathode and a second plurality of closed channels is formed between the first corrugated portion and the second planar portion of said anode; and a DC potential source coupled to said anode and said cathode for applying a DC voltage thereacross for transferring oxygen form an oxygen-bearing gas introduced into said first plurality of closed channels through said solid electrolyte and into said second plurality of closed channels.

2. The oxygen pump of claim 1 wherein said anode and said cathode are each comprised of a porous lanthanum manganite ($LaMnO_3$).

3. The oxygen pump of claim 1 wherein said solid electrolyte is comprised of yttria stabilized zirconia.

4. The oxygen pump of claim 1 wherein said first pluralities of corrugations and closed channels are aligned with and generally parallel to said second plural of corrugations and closed channels.

5. The oxygen pump of claim 1 wherein said first pluralities of corrugations and closed channels are aligned generally transverse to said second pluralities of corrugations and closed channels.

6. The oxygen pump of claim 1 further comprising first and second dense, electrically conductive interconnecting layers coupled to and in electrical contact with the first corrugated portion of said anode and the third corrugated portion of said anode and respectively forming third and fourth pluralities of closed channels therewith, wherein said oxygen-bearing gas is also introduced into said third plurality of closed channels and the oxygen is also transferred into said fourth plurality of closed channels.

7. The oxygen pump of claim 6 wherein said first and second interconnecting layers are comprised of non-porous lanthanum manganite ($LaMnO_3$).

8. The oxygen pump of claim 6 further comprising second and third combinations of a corrugated anode and cathode and a conductive solid electrolyte disposed therebetween in electrical contact with said first and second interconnecting layers, respectively, and coupled to said DC potential source so as to form a stacked array of oxygen pumps.

9. The oxygen pump of claim 8 wherein the first closed channels associated with each cathode and the second closed channels associated with each anode are aligned generally transversely with respect to each other.

10. The oxygen pump of claim 9 further comprising a plurality of manifolds disposed about the lateral periphery of the stacked array of oxygen pumps.

11. The oxygen pump of claim 10 wherein said plurality of manifolds includes an inlet and a first outlet manifold aligned and continuous with said first and third pluralities of closed channels and disposed on facing lateral surfaces of the stacked oxygen pump array for respectively introducing the oxygen-bearing gas into said stacked array and exhausting the oxygen-bearing gas from said stacked array.

12. The oxygen pump of claim 11 wherein said plurality of manifolds further includes a second outlet manifold aligned and continuous with said second and fourth pluralities of closed channels and disposed on a remaining lateral surface of the stacked oxygen pump array for removing the oxygen removed from the oxygen-bearing gas from the stacked oxygen pump array 13. The oxygen pump of claim 12 wherein each of said inlet and outlet manifolds includes a respective gas flow duct therein 14. The oxygen pump of claim 12 further comprising coupling means for securely affixing each of said inlet and outlet manifolds to a respective lateral surface of the stacked oxygen pump array.

15. The oxygen pump of claim 14 wherein said coupling means comprises a ceramic paste.

* * * * *